US012642896B2

(12) United States Patent
Yan et al.

(10) Patent No.:  US 12,642,896 B2
(45) Date of Patent:       Jun. 2, 2026

(54) EASY-POUR WEARABLE BREAST PUMP

(71) Applicant: Zhejiang Carebao Co., Ltd., Ningbo (CN)

(72) Inventors: Jianfeng Yan, Ningbo (CN); Yangchun Li, Ningbo (CN); Yonghao Wang, Ningbo (CN)

(73) Assignee: Zhejiang Carebao Co., Ltd., Ningbo (CN)

( * ) Notice: Subject to any disclaimer, the term of this patent is extended or adjusted under 35 U.S.C. 154(b) by 563 days.

(21) Appl. No.: 18/202,316

(22) Filed: May 26, 2023

(65) Prior Publication Data

US 2024/0374795 A1     Nov. 14, 2024

(30) Foreign Application Priority Data

May 12, 2023   (CN) .......................... 202321145742.4

(51) Int. Cl.
*A61M 1/06*          (2006.01)
(52) U.S. Cl.
CPC ............ *A61M 1/064* (2014.02); *A61M 1/067* (2021.05)
(58) Field of Classification Search
CPC ........ A61M 1/06; A61M 1/064; A61M 1/067; A61M 1/062; A61M 1/65; A61M 1/80; A61M 1/066; A61M 1/82; A61M 2205/075
See application file for complete search history.

(56) References Cited

U.S. PATENT DOCUMENTS

| | | | | |
|---|---|---|---|---|
| 4,263,912 A | * | 4/1981 | Adams ................ | A61M 1/0697 604/75 |
| 4,323,067 A | * | 4/1982 | Adams ................. | A61M 1/062 604/74 |
| 4,759,747 A | * | 7/1988 | Aida ....................... | A61M 1/06 604/74 |
| 2005/0154348 A1 | * | 7/2005 | Lantz ................. | A61M 1/0697 604/74 |

(Continued)

FOREIGN PATENT DOCUMENTS

| | | | | | |
|---|---|---|---|---|---|
| CN | 105233355 A | * | 1/2016 | ............ | A61M 1/062 |
| CN | 109621041 A | * | 4/2019 | ............. | A61M 1/06 |
| CN | 109621044 A | * | 4/2019 | ............. | A61M 1/06 |

(Continued)

OTHER PUBLICATIONS

CN 213432133, English Language Machine Translation (Year: 2021).*

*Primary Examiner* — Wesley G Harris

(57) ABSTRACT

The present disclosure provides an easy-pour wearable breast pump, which includes a milk storage assembly and a host which are mutually detachably connected. The host includes a host housing, a battery and an air pump. The host housing is provided with a first connector. The milk storage assembly includes a milk storage bowl and a seal cap, and the milk storage bowl and the seal cap are connected to form an installation cavity. A suction air bag is installed in the installation cavity. The seal cap is provided with a second connector. The first connector and the second connector are in detachable sealed communicating connection. A milk-pouring port is formed in a top of the milk storage bowl, the suction air bag is not required to be detached during milk pouring, and milk can be poured directly after the host is detached.

14 Claims, 7 Drawing Sheets

(56)                    References Cited

U.S. PATENT DOCUMENTS

2005/0228342 A1 * 10/2005 Yuen ................... A61M 1/0697
                                                                          604/74
2020/0384172 A1 * 12/2020 Kim ...................... A61M 1/064

FOREIGN PATENT DOCUMENTS

CN         111588927  A  *  8/2020   ............ A61M 1/064
CN         213432133  U  *  6/2021
DE           3508410  A1 *  9/1985   .......... A61M 1/0697
EP           3597230  A1 *  1/2020   .......... A61H 9/0057
WO     WO-2011013037  A1 *  2/2011   .............. A61M 1/06

* cited by examiner

EASY-POUR WEARABLE BREAST PUMP

CROSS REFERENCE TO RELATED APPLICATIONS

The present application claims the benefit of Chinese Patent Application No. 202321145742.4 filed on May 12, 2023, the contents of which are incorporated herein by reference in their entirety.

TECHNICAL FIELD

The present disclosure relates to the technical field of mother and baby products, and more particularly relates to an easy-pour wearable breast pump.

BACKGROUND ART

A wearable breast pump is a type of breast pump capable of being fixed onto the breast, and has good portability and privacy. However, for an existing wearable breast pump, it generally needs to remove a suction air bag to pour milk, which is troublesome in operation and unhygienic.

SUMMARY OF THE INVENTION

In order to solve at least one aspect of the above problems, the present disclosure provides an easy-pour wearable breast pump, which includes a milk storage assembly and a host which are mutually detachably connected. The host includes a host housing and a battery and an air pump which are installed in the host housing. The air pump is electrically connected to the battery, and the host housing is provided with a first connector communicating with the air pump. The milk storage assembly includes a milk storage bowl and a seal cap which is in sealed connection with the milk storage bowl, and the milk storage bowl and the seal cap are connected to form an installation cavity. A suction air bag is installed in the installation cavity. The seal cap is provided with a second connector communicating with the suction air bag. The first connector and the second connector are in detachable sealed communicating connection. A milk-pouring port is formed in a top of the milk storage bowl. When the first connector and the second connector are mutually separated, the host is detached from the milk storage assembly, so as to pour milk in the milk storage bowl from the milk-pouring port.

Optionally, during breast pumping operation, a lower surface of the host housing is attached to an upper surface of the seal cap.

Optionally, a groove is formed in the upper surface of the seal cap, an annular boss matched with the groove is formed on the lower surface of the host housing, the first connector is located in the annular boss, and the second connector is located in the groove.

Optionally, an outer wall of the annular boss is sleeved with a rubber ring. During the breast pumping operation, the rubber ring is tightly clamped between an inner wall of the groove and the outer wall of the annular boss.

Optionally, the host housing is provided with a positioning column, and the seal cap is provided with a positioning groove matched with the positioning column.

Optionally, the milk-pouring port is hinged with a cover plate, and during the breast pumping operation, the cover plate covers the milk-pouring port, and during milk pouring operation, the cover plate is opened relative to the milk-pouring port under the action of gravity, so as to pour the milk in the milk storage bowl.

Optionally, an outer wall of the milk storage bowl is provided with a plurality of snap-fit blocks, and the seal cap is provided with snap-fit grooves matched with the snap-fit blocks.

Optionally, an edge of the seal cap is downwards convexly provided with a fool-proof sheet, and the milk storage bowl is provided with a notch for avoiding the fool-proof sheet.

Optionally, the milk storage assembly further includes a breast shield connected to the milk storage bowl. The milk storage bowl is provided with an accommodating cavity used for storing the milk. The accommodating cavity communicates with the breast shield, the installation cavity is located in the outer wall of the milk storage bowl, and the installation cavity is provided with a through hole communicating with the breast shield.

Optionally, the breast shield includes a breast shield inner ring and a breast shield outer ring used for being closely attached to the breast. The milk storage bowl is provided with a connecting column, two ends of the breast shield inner ring are connected to the breast shield outer ring and the connecting column respectively, and the installation cavity communicates with the connecting column through the through hole.

Optionally, the milk storage bowl is provided with an opening, and the breast shield is in sealed connection with the opening to form the accommodating cavity.

Optionally, a side wall of the breast shield inner ring is provided with a milk outlet communicating with the accommodating cavity, and the milk outlet is connected with a one-way valve.

Optionally, a joint of the breast shield inner ring and the breast shield outer ring is provided with an anti-backflow portion.

Compared with the prior art, according to the easy-pour wearable breast pump in the present disclosure, the host and the milk storage assembly are separately arranged, the suction air bag is arranged in the milk storage assembly, the suction air bag does not need to be detached during milk pouring, and the milk can be poured directly after the host is detached. On one hand, the steps of disassembling and assembling the suction air bag in the breast pumping operation process are omitted, thereby improving breast pumping efficiency. On the other hand, the suction air bag is not detached, and the suction air bag can still prevent outside dust and bacteria from entering, through the through hole, the milk storage bowl after the host is detached, which is more hygienic and safer.

DESCRIPTIONS OF REFERENCE NUMERALS

Figure 1:
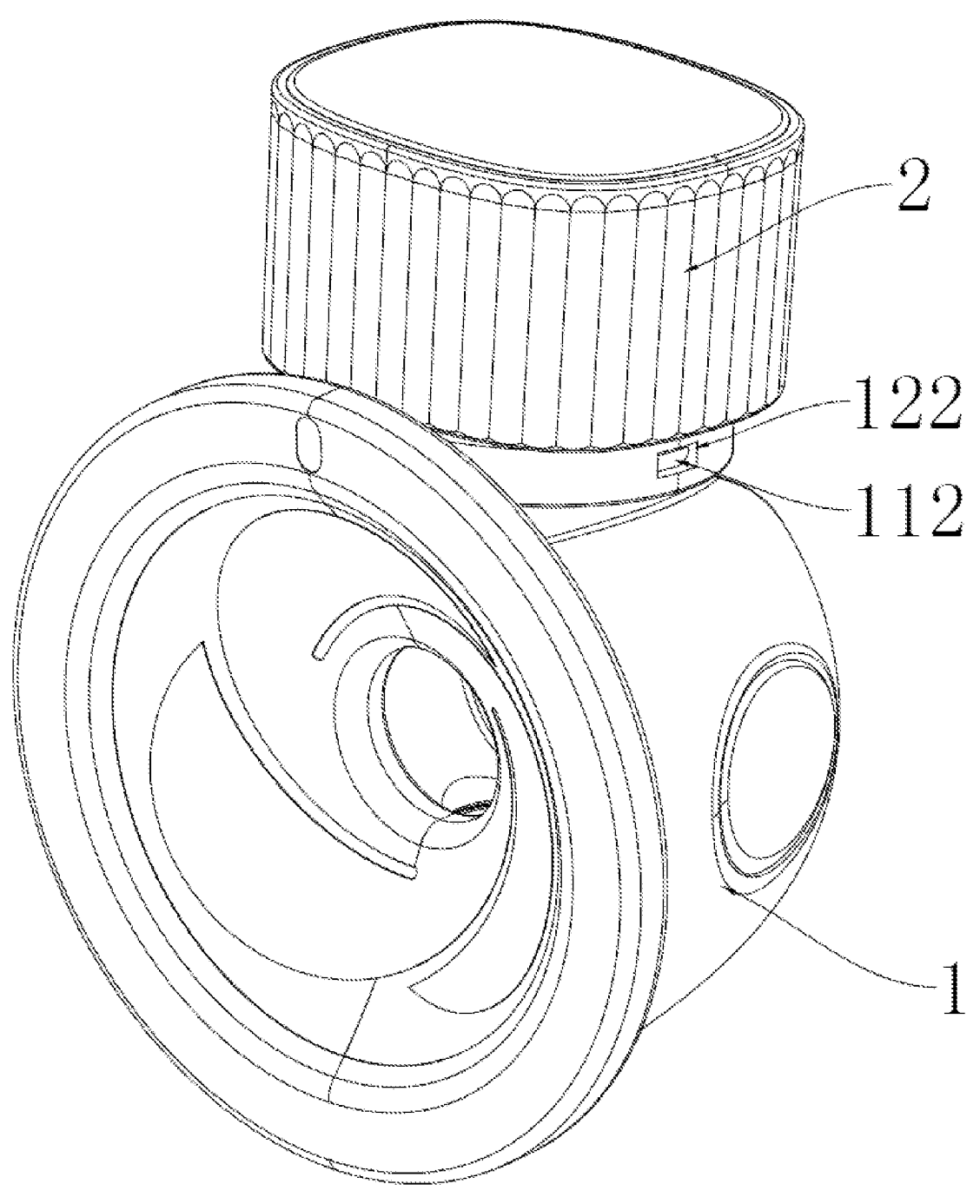
FIG. 1 is a structural diagram of an easy-pour wearable breast pump according to an embodiment of the present disclosure.

1—milk storage assembly; 11—milk storage bowl; 111—milk-pouring port; 112—snap-fit block; 113—accommodating cavity; 114—connecting column; 115—opening; 116—notch; 12—seal cap; 121—second connector; 122—snap-fit groove; 123—fool-proof sheet; 124—groove; 125—positioning groove; 13—installation cavity; 131—through hole; 14—suction air bag; 15—breast shield; 151—breast shield inner ring; 152—breast shield outer ring; 153—milk outlet; 154—anti-backflow portion; 16—one-way valve; 2—host; 21—host housing; 211—first connector; 212—annular boss; 213—positioning column; 22—battery; 23—air pump; and 24—rubber ring.

DETAILED DESCRIPTION OF THE INVENTION

To make the above purposes, characteristics and advantages of the present disclosure more apparent and easier to understand, specific embodiments of the present disclosure are described in detail in combination with the drawings below.

In the description of the present disclosure, it is to be understood that an orientation or position relationship indicated by terms such as "upper" and "lower" is an orientation or position relationship based on normal usage of the product.

Terms "first" and "second" are merely used for describing the purposes but not understood as indicating or implying relative importance or implying to indicate the number of indicated technical features. Thus, features limited with "first" and "second" may explicitly or implicitly include at least one feature.

An embodiment of the present disclosure provides an easy-pour wearable breast pump, which includes, in combination with FIG. 1 to FIG. 5, a milk storage assembly 1 and a host 2 which are mutually detachably connected. The host 2 includes a host housing 21 and a battery 22 and an air pump 23 which are installed in the host housing 21. The air pump 23 is electrically connected to the battery 22, and the host housing 21 is provided with a first connector 211 communicating with the air pump 23. The milk storage assembly 1 includes a milk storage bowl 11 and a seal cap 12 which is in sealed connection with the milk storage bowl 11, and the milk storage bowl 11 and the seal cap 12 are connected to form an installation cavity 13. A suction air bag 14 is installed in the installation cavity 13. The seal cap 12 is provided with a second connector 121 communicating with the suction air bag 14. The first connector 211 and the second connector 121 are in detachable sealed communicating connection. A milk-pouring port 111 is formed in a top of the milk storage bowl 11. When the first connector 211 and the second connector 121 are mutually separated, the host 2 is detached from the milk storage assembly 1, so as to pour milk in the milk storage bowl 11 from the milk-pouring port 111.

During breast pumping operation, the milk storage assembly 1 and the host 2 are mutually connected, and the first connector 211 and the second connector 121 are in interference fit or in threaded connection, which not only ensures sealing performance during connection, but also facilitates mutual detachment of two parts. The first connector 211 is preferably made of silicone materials and is detachably connected to the host housing 21, and the silicone materials have a certain deformation. The second connector 121 is preferably integrally inject-molded with the seal cap 12, and has a certain hardness. When the first connector 211 and the second connector 121 are connected, the first connector 211 made of the silicone materials can be tightly clamped in the second connector 121 with good sealing performance, and in the breast pumping process, the first connector 211 and the second connector 121 become increasingly tight along with continuous suction. The suction air bag 14 is of a bowl-shaped structure, an outer wall of the suction air bag 14 is attached to an inner wall of the installation cavity 13 when there is no suction force, and under the action of suction force, the suction air bag 14 deforms, and accordingly a pressure difference is generated. The installation cavity 13 is formed in the top of the milk storage bowl 11, so as to sufficiently utilize limited space during the wearable breast pumping operation. The air pump 23 is connected to a one-way battery valve used for deflating the air pump 23. The battery 22 is used for supplying power to the one-way battery valve and the air pump 23. During the breast pumping operation, the air pump 23 works and generates a negative pressure, the suction air bag 14 is extruded, such that the pressure difference is generated in the milk storage assembly 1, thereby facilitating milk ejection from the nipple. The one-way battery valve is opened to make the air pump 23 communicate with the outside, the inside pressure intensity and the outside pressure intensity are balanced, such that the suction air bag 14 expands and recovers, and the process is repeatedly performed to realize the breast pumping operation.

The top of the milk storage bowl 11 is provided with the milk-pouring port 111 communicating with the outside. After breast pumping is finished, the host 2 is detached from a milk storage assembly, and then milk in the milk storage bowl 11 can be poured out through the milk-pouring port 111. The hand of a user is not likely to make direct contact with breast milk during the operation, thereby ensuring hygiene of the milk.

According to the easy-pour wearable breast pump in this embodiment, the host 2 and the milk storage assembly 1 are separately arranged, the suction air bag 14 is arranged in the milk storage assembly 1, the suction air bag 14 is not required to be detached during milk pouring, and milk can be poured directly after the host 2 is detached. On one hand, the steps of disassembling and assembling the suction air bag 14 in the breast pumping operation process are omitted, thereby improving breast pumping efficiency. On the other hand, the suction air bag 14 is not detached, so that the suction air bag 14 can still prevent outside dust and bacteria from entering, through a through hole 131, the milk storage bowl 11 after the host 2 is detached, which is more hygienic and safer.

Figure 2:
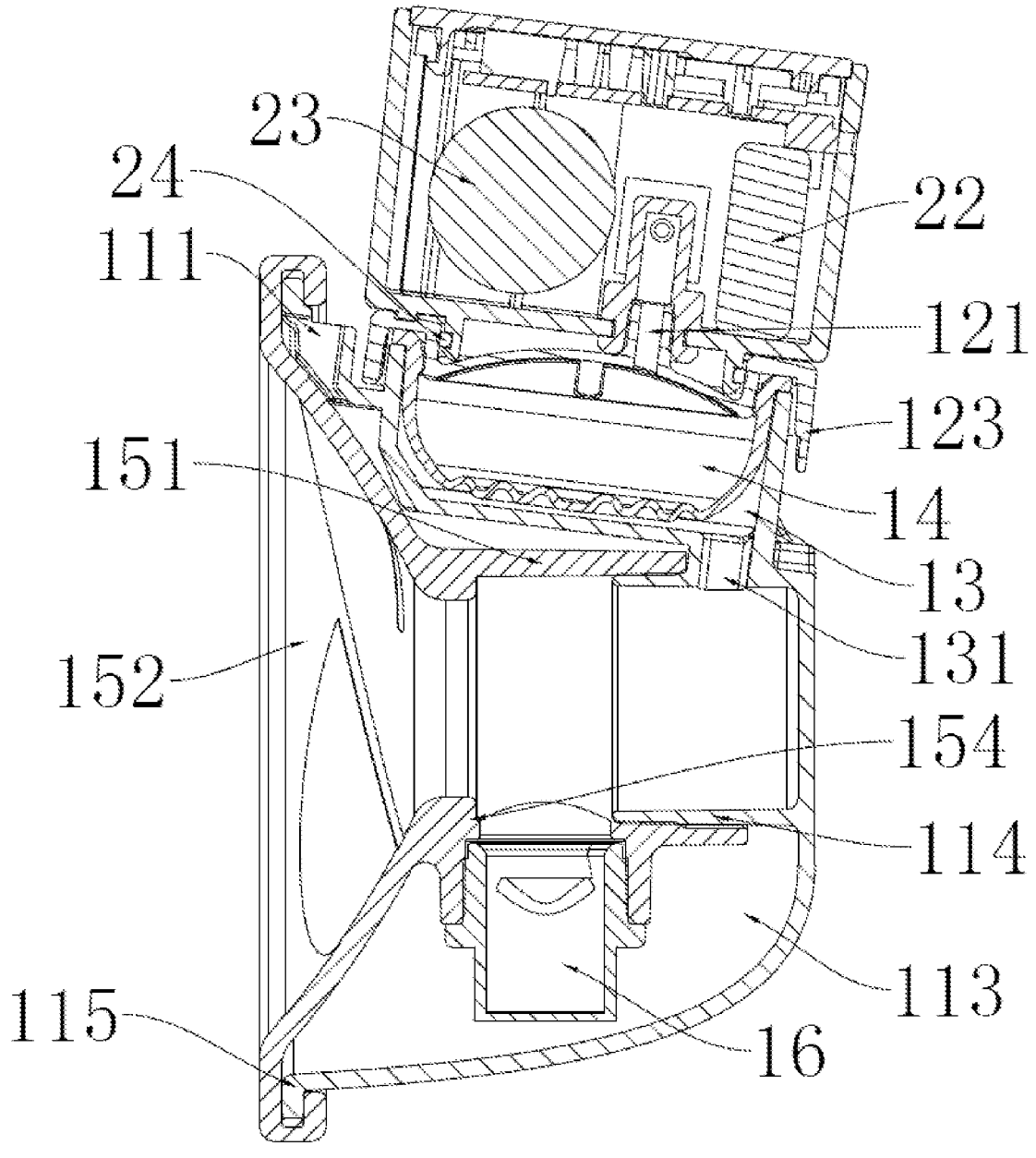
FIG. 2 is a section view of the easy-pour wearable breast pump according to an embodiment of the present disclosure.

Optionally, in combination with FIG. 1 and FIG. 2, during the breast pumping operation, a lower surface of the host housing 21 is attached to an upper surface of the seal cap 12.

The first connector 211 is concave relative to the lower surface of the host housing 21, and the second connector 121 is convex relative to the upper surface of the seal cap 12. During breast pumping, the second connector 121 is inserted in the first connector 211 to realize sealed connection; and the lower surface of the host housing 21 is attached to the upper surface of the seal cap 12, so as to ensure structural compactness.

Optionally, in combination with FIG. 1 to FIG. 5, the upper surface of the seal cap 12 is a plane, and the lower surface of the host housing 21 is a plane; and the structural design of the plane firstly facilitates tight abut joint of the host housing 21 and the seal cap 12, and secondly facilitates cleaning and maintaining of the plane structure. In addition, the upper surface of the seal cap 12 and the lower surface of the host housing 21 may also be curved surfaces.

Optionally, in combination with FIG. 2 to FIG. 5, a groove 124 is formed in the upper surface of the seal cap 12, an annular boss 212 matched with the groove 124 is formed in the lower surface of the host housing 21, the first connector 211 is located in the annular boss 212, and the second connector 121 is located in the groove 124. The groove 124 is matched with the annular boss 212 in shape, and when the host 2 and the milk storage assembly 1 are assembled, an edge surface of the groove 124 is closely attached to the lower surface of the host housing 21, such that an integral structure is compact. A structure that the groove 124 is matched with the annular boss 212 is additionally arranged, such that connection between the host 2 and the milk storage assembly 1 is firmer, thereby ensuring firm connection between the first connector 211 and the second connector 121 in the breast pumping process, and stability during the breast pumping operation.

Figure 5:
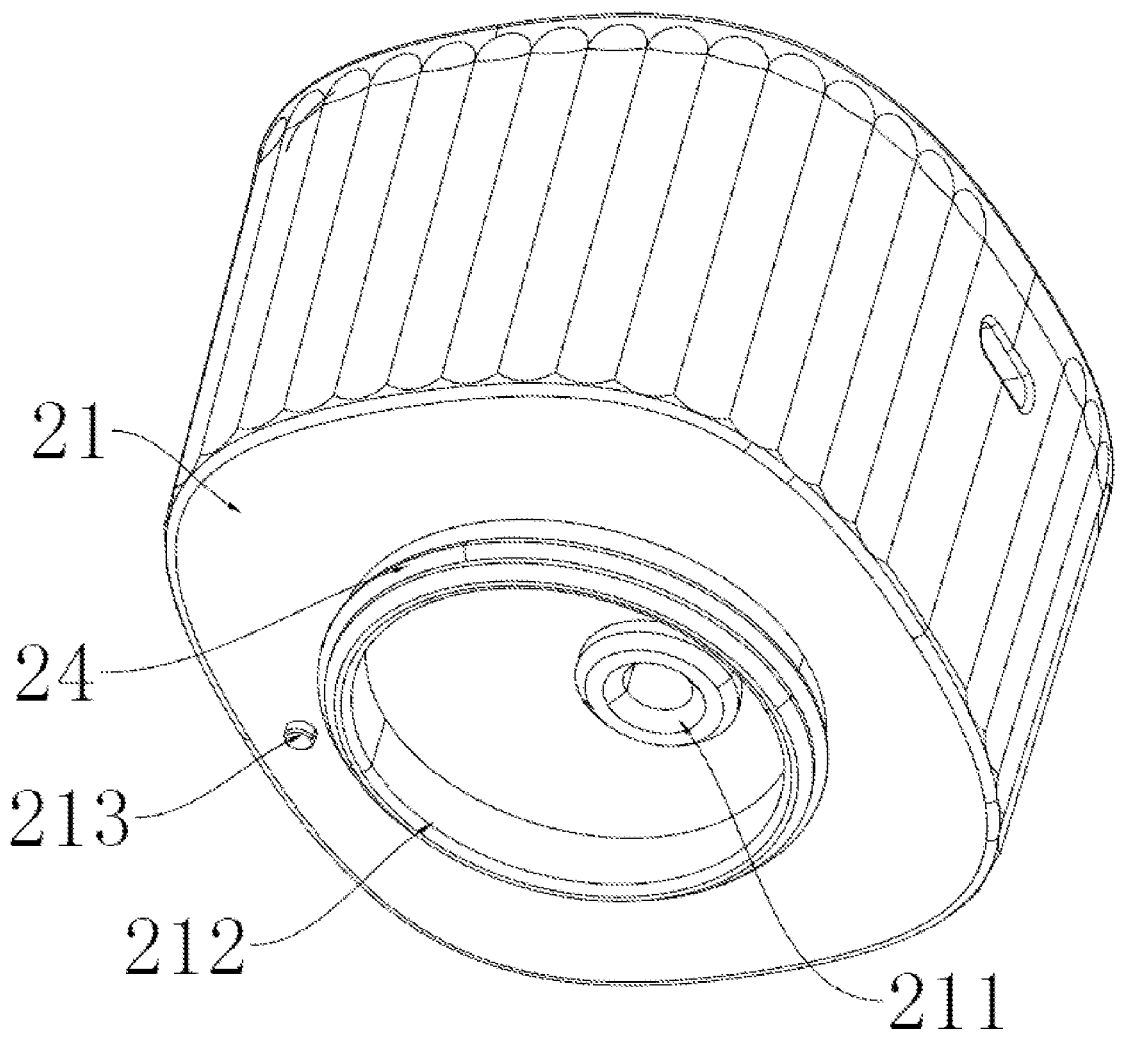
FIG. 5 is a structural diagram of a host according to an embodiment of the present disclosure.

Optionally, in combination with FIG. 2 and FIG. 5, an outer wall of the annular boss 212 is sleeved with a rubber ring 24. During the breast pumping operation, the rubber ring 24 is tightly clamped between an inner wall of the groove 124 and the outer wall of the annular boss 212. The rubber ring 24 is made of silicone, which has certain elasticity. On one hand, the elastic rubber ring 24 can fill a gap between the groove 124 and the annular boss 212, increase friction force between the groove 124 and the annular boss 212, prevent the host 2 from shaking during the breast pumping operation, and avoid noise. On the other hand, the elastic rubber ring 24 can compensate for a size assembly error of the groove 124 and the annular boss 212, and reduce requirements for processing precision.

Optionally, in combination with FIG. 2 to FIG. 5, the host housing 21 is provided with a positioning column 213, and the seal cap 12 is provided with a positioning groove 125 matched with the positioning column 213. When the groove 124 and the annular boss 212 are mutually assembled, through mutual cooperation of the positioning groove 125 and the positioning column 213, the host 2 can be prevented from rotating relative to the milk storage assembly 1, thereby ensuring the stability of the breast pumping process.

Optionally, the milk-pouring port 111 is hinged with a cover plate, and during the breast pumping operation, the cover plate covers the milk-pouring port 111, and during milk pouring operation, the cover plate is opened relative to the milk-pouring port 111 under the action of gravity, so as to pour the milk in the milk storage bowl 11.

One side of the cover plate and an edge of the milk-pouring port 111 are in hinged connection through an accordion fold, and one side of the cover plate and the edge of the milk-pouring port 111 may also be in hinged connection through a matched structure of a pin shaft and a shaft hole. The arrangement of the cover plate can ensure that hygiene inside the milk storage bowl 11 is kept during the breast pumping operation, and prevent dust and the like from entering the milk storage bowl 11. During the milk pouring operation, the breast pumping assembly is overturned, such that the milk-pouring port 111 is arranged upwards, and at the time, the cover plate is opened relative to the milk-pouring port 111 under the action of the gravity, thereby making the milk in the milk storage bowl 11 be poured out.

Figure 6:
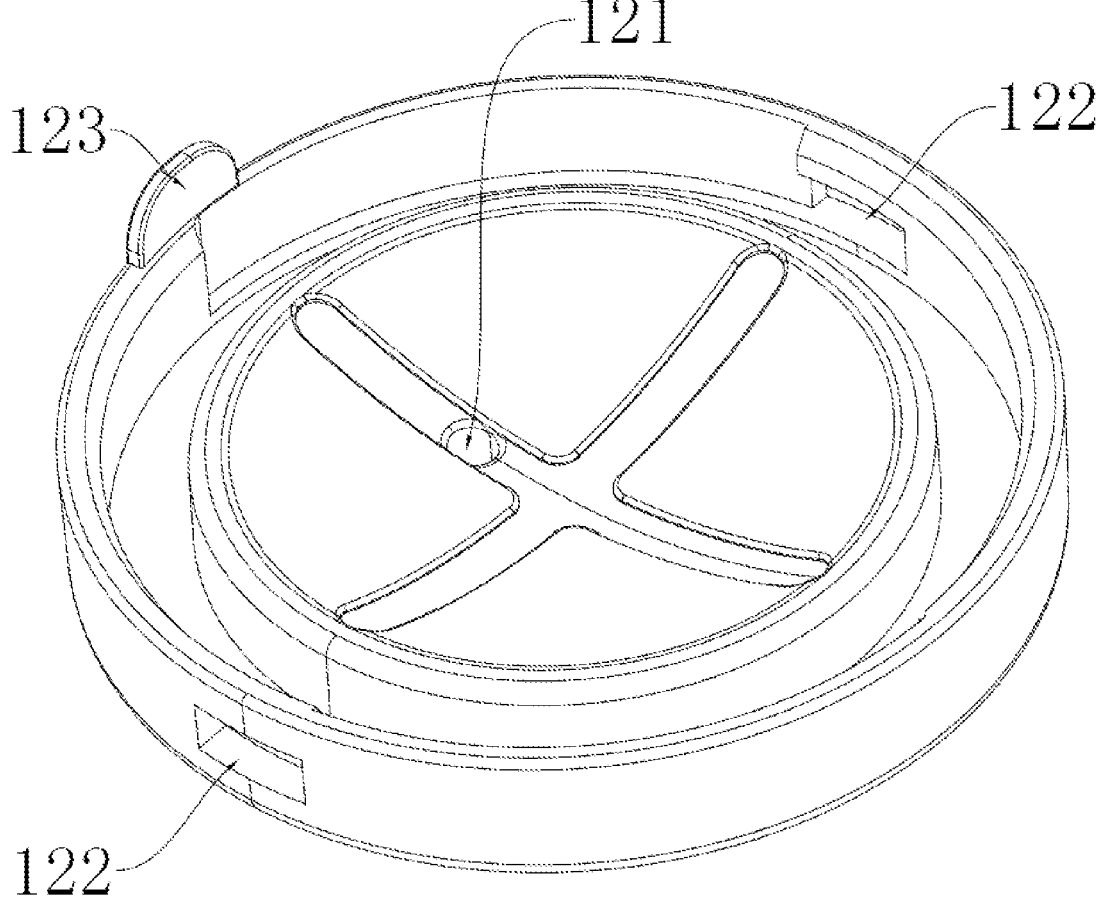
FIG. 6 is a structural diagram of a seal cap according to an embodiment of the present disclosure.
Figure 7:
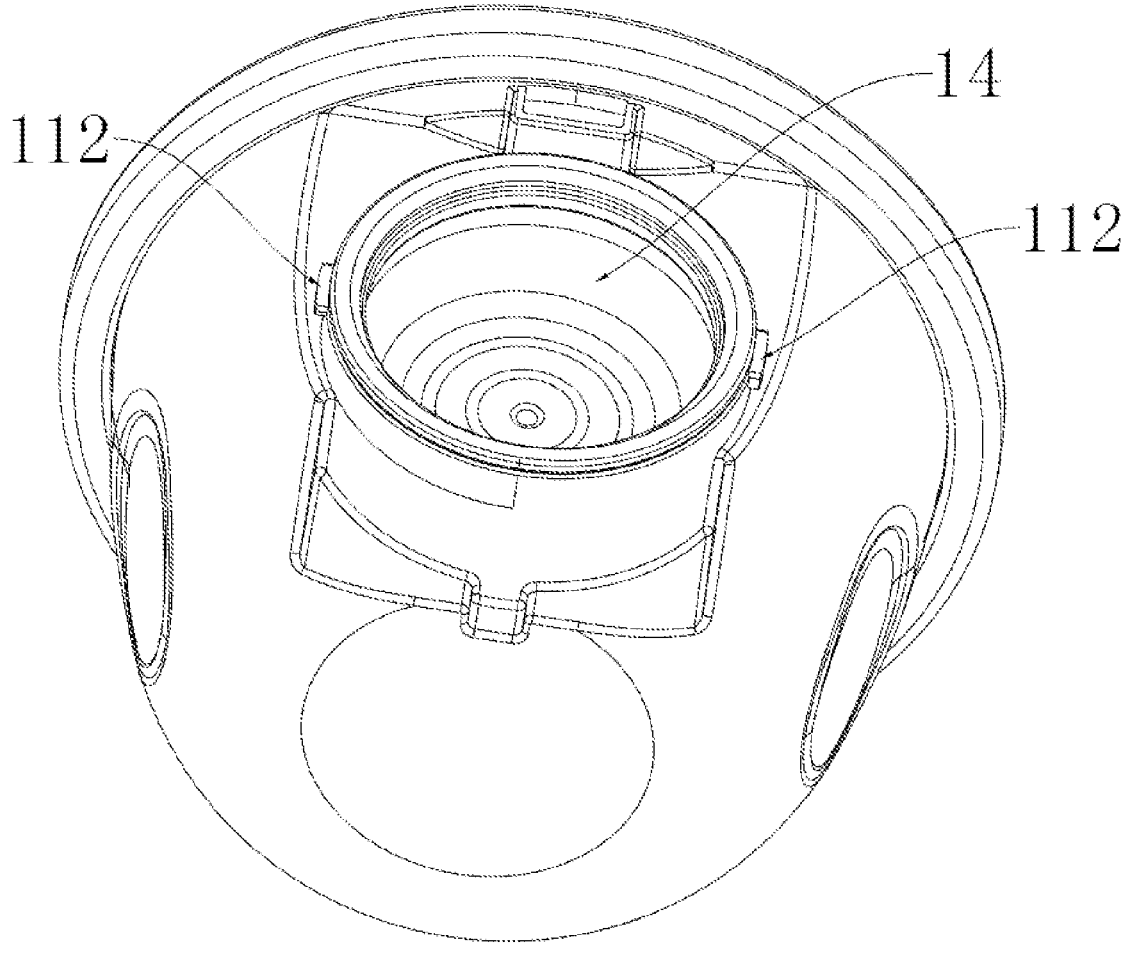
FIG. 7 is a local structural diagram of a milk storage assembly according to an embodiment of the present disclosure.

Optionally, in combination with FIG. 1, FIG. 6 and FIG. 7, an outer wall of the milk storage bowl 11 is provided with a plurality of snap-fit blocks 112. The seal cap 12 is provided with snap-fit grooves 122 matched with the snap-fit blocks 112. By arranging the snap-fit blocks 112 and the snap-fit grooves 122 which are rotationally in snap joint, the seal cap 12 and the milk storage bowl 11 can be convenient to disassemble and assemble.

Figure 4:
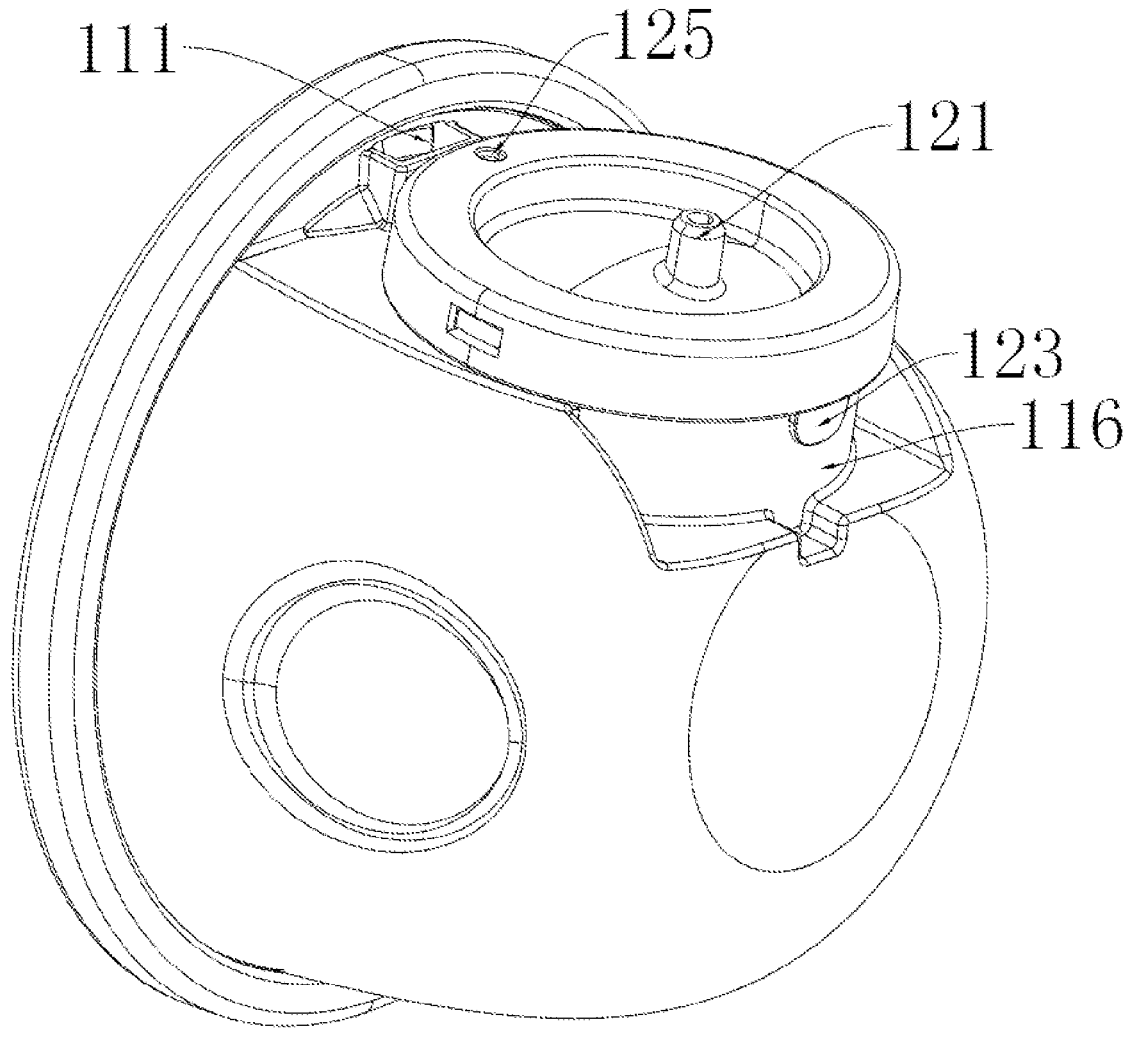
FIG. 4 is a second structural diagram of the breast pumping assembly according to an embodiment of the present disclosure.

Optionally, in combination with FIG. 2, FIG. 4 and FIG. 6, an edge of the seal cap 12 is downwards convexly provided with a fool-proof sheet 123. The milk storage bowl 11 is provided with a notch 116 for avoiding the fool-proof sheet 123. The notch 116 has a large space, such that the fool-proof sheet 123 has an enough movement space when the seal cap 12 is in rotational snap fit relative to the milk storage bowl 11. By arranging the fool-proof sheet 123, the fool-proof sheet 123 can only be installed at the notch 116, such that the seal cap 12 can only be assembled with the milk storage bowl 11 at the assigned position, thereby ensuring the fixed position of the second connector 121, preventing position assembly errors, and then ensuring smooth butt joint between the second connector 121 and the first connector 211.

Figure 3:
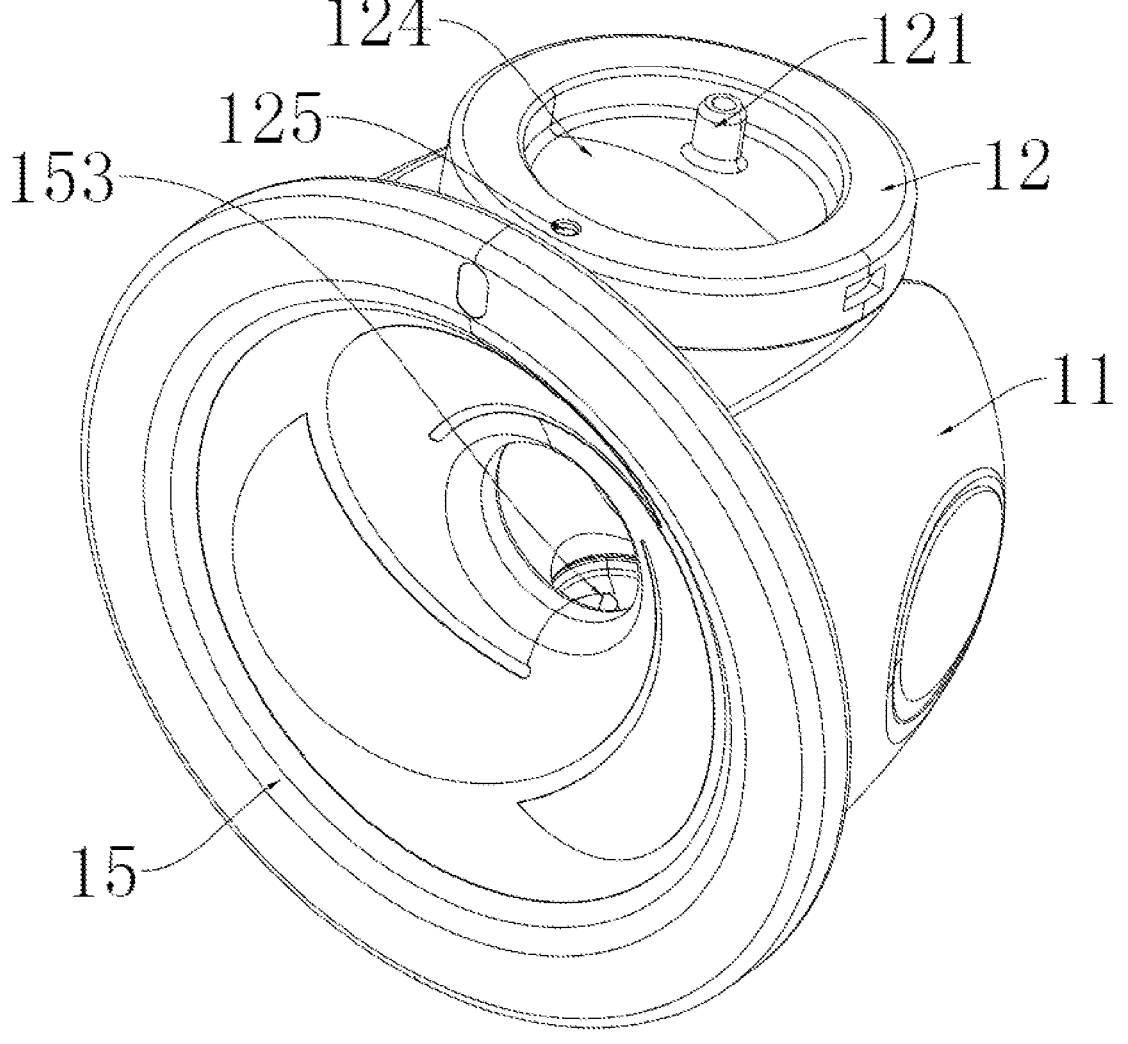
FIG. 3 is a first structural diagram of a breast pumping assembly according to an embodiment of the present disclosure.

Optionally, in combination with FIG. 1, FIG. 2 and FIG. 3, the milk storage assembly 1 further includes a breast shield 15 connected to the milk storage bowl 11. The milk storage bowl 11 is provided with an accommodating cavity 113 used for storing the milk. The accommodating cavity 113 communicates with the breast shield 15, the installation cavity 13 is located in the outer wall of the milk storage bowl 11, and the installation cavity 13 is provided with the through hole 131 communicating with the breast shield 15.

The through hole 131 is formed in a bottom of the installation cavity 13, during breast pumping, a horn mouth of the breast shield 15 is closely attached to the breast, and at the time, the installation cavity 13, the breast shield 15 and the milk storage bowl 11 can be in sealed communication. When the suction air bag 14 deforms, the nipple is pulled by the pressure difference to eject milk, and finally, the sucked milk flows, through the breast shield 15, into the milk storage bowl 11 to be stored.

The breast shield 15 is made of food-grade liquid silicone, and makes direct contact with the breast, the material is soft, does not harm the skin and can ensure usage comfort, and during usage, fit is more closely, so as to prevent phenomena of air leakage and milk backflow. A surface of the breast shield 15 is provided with fine textures, which can increase friction force between the breast shield 15 and the breast of a user. The suction air bag 14 is preferably made of silicone, which has certain elasticity so as to deform under stress.

In this embodiment, the installation cavity 13 is formed in an outer portion of the milk storage bowl 11, which greatly reduces assembly difficulty between the suction air bag 14 and the milk storage bowl 11, and makes the suction air bag 14 smoothly connected to the installation cavity 13 in a sealed manner, thereby ensuring that air leakage cannot happen during the breast pumping operation, and improving breast pumping efficiency.

Optionally, in combination with FIG. 1 and FIG. 2, the breast shield 15 includes a breast shield inner ring 151 and a breast shield outer ring 152 used for being closely attached to the breast. The milk storage bowl 11 is provided with a connecting column 114, two ends of the breast shield inner ring 151 are connected to the breast shield outer ring 152 and the connecting column 114 respectively, and the installation cavity 13 communicates with the connecting column 114 through the through hole 131.

The connecting column 114 is arranged on the side, away from the breast shield outer ring 152, in the accommodating cavity 113, such that the breast pump is more compact in structure in a forward and backward direction, and the connecting column 114 and the milk storage bowl 11 are integrally formed. The breast shield outer ring 152 and the breast shield inner ring 151 are integrally formed, and the connecting column 114 and the breast shield inner ring 151 are in sealed connection, thereby ensuring sealing performance of the breast shield 15 and making a breast pumping effect better.

Optionally, in combination with FIG. 1, FIG. 2 and FIG. 3, the milk storage bowl 11 is provided with an opening 115. The breast shield 15 is in sealed connection with the opening 115 to form the accommodating cavity 113, that is, the breast shield 15 is utilized as one wall of the accommodating cavity 113 so as to sufficiently utilize the structure of the breast shield 15, such that the integral structure is more compact. The milk storage space may be expanded to the periphery of the inner surface of the breast shield 15, and thus, the milk storage space is greatly enlarged.

Optionally, in combination with FIG. 2 and FIG. 3, a side wall of the breast shield inner ring 151 is provided with a milk outlet 153 communicating with the accommodating cavity 113, and the milk outlet 153 is connected with a one-way valve 16.

The breast milk enters the one-way valve 16 from the milk outlet 153 of the breast shield inner ring 151, and enters the milk storage bowl 11 through the one-way valve 16, and the one-way valve 16 can prevent the milk in the milk storage bowl 11 from flowing back into the breast shield 15. The one-way valve 16 and the milk outlet 153 can be mutually detachably connected, such that cleaning operation is facilitated after detachment. In this embodiment, the one-way valve 16 is assembled to the breast shield 15, such that the breast pump is convenient to disassemble and assemble, and the sealing effect is good.

Optionally, in combination with FIG. 2 and FIG. 3, a joint of the breast shield inner ring 151 and the breast shield outer ring 152 is provided with an anti-backflow portion 154.

The anti-backflow portion 154 is located above the milk outlet 153, and the anti-backflow portion 154 is an annular portion formed after a tail end of the breast shield outer ring 152 extends towards the breast shield inner ring 151, and the tail end of the breast shield outer ring 152 refers to the end connected to the breast shield inner ring 151. After the milk enters the breast shield inner ring 151, the milk flows into the milk outlet 153 under the action of the gravity, and when the user lies flat or lies on one side for breast pumping, the anti-backflow portion 154 can prevent the milk in the breast shield inner ring 151 from flowing back to the breast shield outer ring 152. It should be noted that the lying posture herein refers to that the upper body of the user upwards tilts by a small angle, preferably by 30 degrees, so as to ensure that the milk in the breast shield inner ring 151 cannot flow back.

In this embodiment, the anti-backflow portion 154 is arranged, such that the user can lie flat or lie on one side for breast pumping besides sitting for breast pumping, thereby achieving the purpose of different-angle breast pumping. Operation is convenient, and application scenarios are wide.

The present disclosure is disclosed above, but the scope of protection of the present disclosure is not limited thereto.

Those skilled in the art can make various changes and modifications without departing from the spirit and scope of the present disclosure, and all such changes and modifications shall fall within the scope of protection of the present disclosure.

What is claimed is:

1. An easy-pour wearable breast pump, comprising a milk storage assembly (1) and a host (2) which are mutually detachably connected, wherein the host (2) comprises a host housing (21) and a battery (22) and an air pump (23) which are installed in the host housing (21), the air pump (23) is electrically connected to the battery (22), and the host housing (21) is provided with a first connector (211) communicating with the air pump (23); the milk storage assembly (1) comprises a milk storage bowl (11) and a seal cap (12) which is in sealed connection with the milk storage bowl (11), the milk storage bowl (11) and the seal cap (12) are connected to form an installation cavity (13), a suction air bag (14) is installed in the installation cavity (13), the seal cap (12) is provided with a second connector (121) communicating with the suction air bag (14), and the first connector (211) and the second connector (121) are in detachable sealed communicating connection; and a milk-pouring port (111) is formed in a top of the milk storage bowl (11), and when the first connector (211) and the second connector (121) are mutually separated, the host (2) is detached from the milk storage assembly (1), so as to pour milk in the milk storage bowl (11) from the milk-pouring port (111);

wherein a groove (124) is formed in an upper surface of the seal cap (12), an annular boss (212) matched with the groove (124) is formed on a lower surface of the host housing (21), the first connector (211) is located in the annular boss (212), and the second connector (121) is located in the groove (124).

2. The easy-pour wearable breast pump according to claim 1, wherein during breast pumping operation, a lower surface of the host housing (21) is attached to an upper surface of the seal cap (12).

3. The easy-pour wearable breast pump according to claim 1, wherein an outer wall of the annular boss (212) is sleeved with a rubber ring (24), and during breast pumping operation, the rubber ring (24) is tightly clamped between an inner wall of the groove (124) and the outer wall of the annular boss (212).

4. The easy-pour wearable breast pump according to claim 1, wherein the host housing (21) is provided with a positioning column (213), and the seal cap (12) is provided with a positioning groove (125) matched with the positioning column (213).

5. The easy-pour wearable breast pump according to claim 1, wherein the milk-pouring port (111) is hinged with a cover plate, and during breast pumping operation, the cover plate covers the milk-pouring port (111), and during milk pouring operation, the cover plate is opened relative to the milk-pouring port (111) under the action of gravity, so as to pour the milk in the milk storage bowl (11).

6. The easy-pour wearable breast pump according to claim 1, wherein an outer wall of the milk storage bowl (11) is provided with a plurality of snap-fit blocks (112), and the seal cap (12) is provided with snap-fit grooves (122) matched with the snap-fit blocks (112).

7. The easy-pour wearable breast pump according to claim 1, wherein an edge of the seal cap (12) is downwards convexly provided with a fool-proof sheet (123), and the milk storage bowl (11) is provided with a notch (116) for avoiding the fool-proof sheet (123).

8. The easy-pour wearable breast pump according to claim 1, wherein the milk storage assembly (1) further comprises a breast shield (15) connected to the milk storage bowl (11), the milk storage bowl (11) is provided with an accommodating cavity (113) used for storing the milk, the accommodating cavity (113) communicates with the breast shield (15), the installation cavity (13) is located in an outer wall of the milk storage bowl (11), and the installation cavity (13) is provided with a through hole (131) communicating with the breast shield (15).

9. The easy-pour wearable breast pump according to claim 8, wherein the breast shield (15) comprises a breast shield inner ring (151) and a breast shield outer ring (152) used for being closely attached to the breast, the milk storage bowl (11) is provided with a connecting column (114), two ends of the breast shield inner ring (151) are connected to the breast shield outer ring (152) and the connecting column (114) respectively, and the installation cavity (13) communicates with the connecting column (114) through the through hole (131).

10. The easy-pour wearable breast pump according to claim 9, wherein a side wall of the breast shield inner ring (151) is provided with a milk outlet (153) communicating with the accommodating cavity (113), and the milk outlet (153) is connected with a one-way valve (16).

11. The easy-pour wearable breast pump according to claim 9, wherein a joint of the breast shield inner ring (151) and the breast shield outer ring (152) is provided with an anti-backflow portion (154).

12. The easy-pour wearable breast pump according to claim 8, wherein the milk storage bowl (11) is provided with an opening (115), and the breast shield (15) is in sealed connection with the opening (115) to form the accommodating cavity (113).

13. An easy-pour wearable breast pump, comprising a milk storage assembly (1) and a host (2) which are mutually detachably connected, wherein the host (2) comprises a host housing (21) and a battery (22) and an air pump (23) which are installed in the host housing (21), the air pump (23) is electrically connected to the battery (22), and the host housing (21) is provided with a first connector (211) communicating with the air pump (23); the milk storage assembly (1) comprises a milk storage bowl (11) and a seal cap (12) which is in sealed connection with the milk storage bowl (11), the milk storage bowl (11) and the seal cap (12) are connected to form an installation cavity (13), a suction air bag (14) is installed in the installation cavity (13), the seal cap (12) is provided with a second connector (121) communicating with the suction air bag (14), and the first connector (211) and the second connector (121) are in detachable sealed communicating connection; and a milk-pouring port (111) is formed in a top of the milk storage bowl (11), and when the first connector (211) and the second connector (121) are mutually separated, the host (2) is detached from the milk storage assembly (1), so as to pour milk in the milk storage bowl (11) from the milk-pouring port (111);

wherein the milk-pouring port (111) is hinged with a cover plate, and during breast pumping operation, the cover plate covers the milk-pouring port (111), and during milk pouring operation, the cover plate is opened relative to the milk-pouring port (111) under the action of gravity, so as to pour the milk in the milk storage bowl (11).

14. An easy-pour wearable breast pump, comprising a milk storage assembly (1) and a host (2) which are mutually detachably connected, wherein the host (2) comprises a host housing (21) and a battery (22) and an air pump (23) which are installed in the host housing (21), the air pump (23) is electrically connected to the battery (22), and the host housing (21) is provided with a first connector (211) communicating with the air pump (23); the milk storage assembly (1) comprises a milk storage bowl (11) and a seal cap (12) which is in sealed connection with the milk storage bowl (11), the milk storage bowl (11) and the seal cap (12) are connected to form an installation cavity (13), a suction air bag (14) is installed in the installation cavity (13), the seal cap (12) is provided with a second connector (121) communicating with the suction air bag (14), and the first connector (211) and the second connector (121) are in detachable sealed communicating connection; and a milk-pouring port (111) is formed in a top of the milk storage bowl (11), and when the first connector (211) and the second connector (121) are mutually separated, the host (2) is detached from the milk storage assembly (1), so as to pour milk in the milk storage bowl (11) from the milk-pouring port (111);

wherein an edge of the seal cap (12) is downwards convexly provided with a fool-proof sheet (123), and the milk storage bowl (11) is provided with a notch (116) for avoiding the fool-proof sheet (123).

* * * * *